(12) United States Patent
Moilanen et al.

(10) Patent No.: US 11,253,435 B2
(45) Date of Patent: Feb. 22, 2022

(54) SECURING POCKET FOR LOOSE PORTION OF MEDICAL TUBING

(71) Applicant: Tubie Pockets, LLC, Jackson, MI (US)

(72) Inventors: Rebekah Lauren Moilanen, Jackson, MI (US); Jeanette Louise Williams, Mason, MI (US)

(73) Assignee: Tubie Pockets LLC, Jackson, MI (US)

( * ) Notice: Subject to any disclaimer, the term of this patent is extended or adjusted under 35 U.S.C. 154(b) by 307 days.

(21) Appl. No.: 16/489,442

(22) PCT Filed: Mar. 1, 2018

(86) PCT No.: PCT/US2018/020360
§ 371 (c)(1),
(2) Date: Aug. 28, 2019

(87) PCT Pub. No.: WO2018/160784
PCT Pub. Date: Sep. 7, 2018

(65) Prior Publication Data
US 2020/0016041 A1    Jan. 16, 2020

Related U.S. Application Data

(60) Provisional application No. 62/465,912, filed on Mar. 2, 2017.

(51) Int. Cl.
*A61J 15/00* (2006.01)
*A41D 27/20* (2006.01)
(Continued)

(52) U.S. Cl.
CPC ...... *A61J 15/0057* (2013.01); *A41D 13/1272* (2013.01); *A41D 27/202* (2013.01);
(Continued)

(58) Field of Classification Search
CPC .............. A61M 39/08; A61M 25/02; A61M 2025/0206; A61J 15/0053; A61J 15/0057;
(Continued)

(56) References Cited

U.S. PATENT DOCUMENTS

| 223,789 A | 1/1880 | Williamson |
|---|---|---|
| 1,129,485 A | 2/1915 | Harman |

(Continued)

FOREIGN PATENT DOCUMENTS

| CA | 2273076 A1 | 12/1999 |
|---|---|---|
| EP | 0045236 A2 | 2/1982 |

*Primary Examiner* — Bhisma Mehta
*Assistant Examiner* — John J Crawford
(74) *Attorney, Agent, or Firm* — Endurance Law Group PLC

(57) ABSTRACT

A securing pocket for managing the loose portion of a medical tube, such as a Nasogastric/Nasojejunal tube, while an implanted portion of the medical tube remains attached to the patient. The loose portion of the medical tube has a coiled section disposed within a receptacle formed between flexible front and rear panels. An integral flap overlaps the front panel to selectively close the receptacle and may be secured with a snap connector. Jam cleats are located along left and right edges adjacent a top edge of the receptacle. Each jam cleat forms a breach in the receptacle through which a tethered section of the loose medical tube extends. The jam cleats are configured to apply a progressive wedge force on the tethered section of the loose medical tube in response to tension along the tube. The jam cleat has flexible sides formed in a V-shape.

20 Claims, 5 Drawing Sheets

(51) Int. Cl.
*A45F 5/02* (2006.01)
*A61M 39/08* (2006.01)
*A61M 25/02* (2006.01)
*A41D 13/12* (2006.01)
*A45F 3/16* (2006.01)

(52) U.S. Cl.
CPC .............. *A41D 27/208* (2013.01); *A45F 5/02* (2013.01); *A45F 2003/166* (2013.01); *A61J 15/0003* (2013.01); *A61J 15/0061* (2013.01); *A61M 39/08* (2013.01); *A61M 2025/0206* (2013.01)

(58) Field of Classification Search
CPC ..... A61J 15/0061; A45F 5/02; A45F 2200/05; A41D 13/1236; A41D 13/1272; A41D 27/202; A41D 27/208; Y10T 24/13; Y10T 24/1414; Y10T 24/39
See application file for complete search history.

(56) References Cited

U.S. PATENT DOCUMENTS

| | | | |
|---|---|---|---|
| 3,648,703 A | 3/1972 | Manker | |
| 4,666,432 A | 5/1987 | McNeish et al. | |
| 4,738,661 A | 4/1988 | Marut | |
| 4,796,790 A | 1/1989 | Hamilton | |
| 5,237,838 A | 8/1993 | Merritt-Munson | |
| 5,295,964 A | 3/1994 | Gauthier | |
| 5,361,603 A | 11/1994 | Merritt-Munson | |
| 5,403,285 A | 4/1995 | Roberts | |
| 5,605,546 A | 2/1997 | Wolzinger et al. | |
| 5,755,698 A | 5/1998 | Kagan et al. | |
| 5,893,370 A | 4/1999 | Perez et al. | |
| 6,065,659 A | 5/2000 | Faz | |
| 6,279,580 B1 | 8/2001 | Perez et al. | |
| 6,296,164 B1 | 10/2001 | Russo | |
| 6,516,981 B2 | 2/2003 | Perez et al. | |
| 6,540,724 B1 | 4/2003 | Harris | |
| 6,579,268 B1 | 6/2003 | Loining | |
| 6,681,404 B1 * | 1/2004 | Adlard | A41D 13/1245 2/94 |
| D636,075 S * | 4/2011 | Yacoub | D24/118 |
| 8,028,834 B2 | 10/2011 | Lill | |
| 8,157,782 B2 | 4/2012 | Marak et al. | |
| 9,775,781 B2 | 10/2017 | Wheeler et al. | |
| 9,775,971 B2 | 10/2017 | Hidalgo | |
| 2002/0113101 A1 | 8/2002 | Skillern | |
| 2005/0033241 A1 | 2/2005 | Hottinger | |
| 2006/0006097 A1 | 1/2006 | Peacock | |
| 2009/0054844 A1 | 2/2009 | Alyea et al. | |
| 2009/0205991 A1 * | 8/2009 | Lill | B65H 75/362 206/438 |
| 2010/0282807 A1 | 11/2010 | Sisk et al. | |
| 2011/0034877 A1 | 2/2011 | Salerno | |
| 2011/0319828 A1 | 12/2011 | Starnes | |
| 2014/0144437 A1 | 5/2014 | Miller | |
| 2014/0196189 A1 | 7/2014 | Lee et al. | |
| 2015/0257463 A1 * | 9/2015 | Trimble | A41D 13/1236 2/48 |
| 2015/0343185 A1 | 12/2015 | Christensen | |
| 2016/0050995 A1 | 2/2016 | Bentley et al. | |

* cited by examiner

SECURING POCKET FOR LOOSE PORTION OF MEDICAL TUBING

CROSS REFERENCE TO RELATED APPLICATIONS

This application claims priority to Provisional Patent Application 62/465,912 filed on Mar. 2, 2017, the entire disclosure of which is hereby incorporated by reference and relied upon.

BACKGROUND OF THE INVENTION

Field of the Invention. The invention relates generally to storing a loose portion of a medical tube against the body of a patient while an implanted or inserted portion of the medical tube remains attached to the patient's body, and more particularly to securing Nasogastric and Nasojejunal tubes.

Description of Related Art. Medical grade tubes are used in many different applications. Common examples of medical tubing include those adapted for intravenous therapy, catheters and Nasogastric/Nasojejunal (NG/NJ) tubes used to feed medical patients who are unable to chew food or swallow. Catheters can be inserted into various locations of the body to drain fluids or to distend body passages. In the case of a NG/NJ tube, the implanted portion is inserted through the nose, passes through the throat and terminates in either the stomach (NG tube) or the jejunum at the beginning of the small intestine (NJ tube). Intravenous therapy, catheters and NG/NJ tubes are but a few of the many examples of medical tubes of relevance to this invention.

In the specific example of NG and NJ tubes, the insertion process is extremely uncomfortable; often the patient must be physically restrained before tubes are placed. Similar discomfort may arise in the placement of other types of medical tubes. For this reason, it is common and humane to leave the implanted portion of a NG/NJ tube inserted in the patient in-between feedings. Meanwhile, the other end of the NG/NJ tube that had been connected to a feed bag, syringe or other feeding source is disconnected and becomes a loose portion. That is to say, the loose portion of a medical tube is that part which is temporarily disconnected from a medical supply or medical device while the other implanted portion of the medical tube remains inside the patient's body.

The loose portion of a medical tube can be a serious nuisance. One such nuisance is the propensity for the loose portion to accidentally snag and catch on objects. NG/NJ tubes and many other types of medical tubes may be lubricated to facilitate the already unpleasant insertion process. This residual lubrication and/or the body's natural production of mucous around a medical tube, makes the medical tube surprisingly easy to remove. Thus, an unexpected snag or catch can tug on the tube can cause the implanted portion to partially or fully withdraw from its implanted position. When this occurs, the patient must endure an uncomfortable re-insertion of the implanted portion of the medical tube.

Because of the ease with which the implanted portion of a medical tube can be inadvertently pulled out of position, it is common to secure the implanted portion of the tube with medical-grade adhesive tape near to the site of insertion. In the case of NG/NJ tubes entering through the nose, any one or multiple forms of medical tape are secured to the patient's cheek like that shown in FIG. 1. Medical-grade adhesive tape is extremely sticky; special adhesive remover is usually required to gently remove the adhesive. When the loose portion of the medical tube is unintentionally yanked due to a snag or pull, a corresponding pull will be felt on the patient's skin through the adhesive. A sufficiently hard pull can tear the patient's skin. Facial skin is tender even for adults, but the facial skin of a young child is especially susceptible to injury under medical-grade adhesive.

It is difficult to overstate the potential for patient harm caused by an inadequately restrained loose portion of medical tube when the implanted portion of the medical tube remains attached to the patient's body. Especially in the case of young patients when the medical tube is a NG/NJ tube whose loose portion hangs from the cheek. Such tubes are constantly being removed accidentally without proper adhesive remover, causing the tape to tear the patient's skin, sometimes causing nausea during removal, and sometimes causing bleeding and even scarring of the cheeks as well as exposing the newly torn wound to possible infection. For patients with compromised immune systems, these repeated tears and exposures create additional complications as germs are introduced into the blood stream.

Furthermore, the access port of a NG/NJ tube (located at the distal tip of the loose portion where feeds or syringes for medicine are inserted) stretches over time and can open suddenly, spilling medicine, food and/or stomach contents. As a result, the loose portion of a medical tube can be leaky and messy.

Finally, there is a common uneasiness faced with handling or holding an infant or small child who has about 18 inches of medical tube (i.e., the loose portion) hanging from his or her cheek or other part of the body. Average non-medically trained adults experience acute anxiety from the fear of possibly tangling or snagging the loose portion of a medical tube (e.g., a NG/NJ tube). A typical result is that it becomes difficult to find an occasional babysitter who is comfortable sitting for a child that has an NG/NJ tube. Without the regular breaks provided by occasional babysitters, parent caregiver fatigue rises. The sad truth is that some caregivers of children fitted with a NG/NJ tube do not have the opportunity to receive a break for even a few minutes to give their tired arms and back a needed rest. The un-secured loose portion of the medical tube is a direct cause of these burdens for patients and caregivers alike.

In hospitals, attempts are made to coil the loose portion of a medical tube around a large safety pin and attach it to the patient's clothing. Unfortunately, most medical tubes are highly resilient and want to uncoil. The lone safety pin is therefore not well-suited to controlling a coiled loose portion of medical tube. In addition, the exposed windings of a medical tube are easily tangled with other medical lines and/or represent an attractive nuisance to young patients tempted to touch and chew. Indeed, these are but a few of the many potential scenarios of concern with the safety pin retention method of controlling a medical tube. Alternatively, hospital staff sometimes tape the loose portion of a medical tube directly to the patient's clothing. This method is cumbersome, can lead to clothing damage and is considered generally inadequate.

Various strap devices have been proposed to hold medical tubes to the patient's clothing but in practice are about as effective as tape or a lone safety pin. Almost invariably with these strap devices, the loose portion of tube is exposed to catch on objects, unwind and invite small hands to touch or little mouths to chew at the tube. For example, U.S. Pat. No. 4,666,432 to McNeish describes a halter top style support that is fitted with a pocket to retain the coiled end of a catheter tube. The pocket is stitched across the bottom and two sides leaving an open top edge like a typical shirt pocket. A button-snap is centered along the open top edge. A slit in the rear panel of the pocket allows the tube to pass through.

U.S. Pat. No. 6,540,724 to Harris describes an animal-shaped pocket for retaining the loose portion of a catheter tube. The pocket is stitched across around three sides leaving an open top edge. Hook-and-loop strips along the top edge provide closure and also frictionally secure the tube so that the pocket is freely suspended, and no external attachment means are necessary. This product is thus not intended to be attached to a patient's clothing, rendering it unable to solve the problem of the tube being dislodged or pulled out completely.

There is therefore a need in the art for an improved apparatus and methods for storing the loose portion of a medical tube while an implanted portion of the medical tube remains attached to the patient's body.

BRIEF SUMMARY OF THE INVENTION

According to a first aspect of this invention, a securing pocket is disclosed for managing the loose portion of a medical tube while the implanted portion of the medical tube remains attached to the patient's body. The securing pocket comprises a receptacle formed between a flexible front panel and a flexible rear panel. The receptacle has left and right and top and bottom edges. The front and rear panels are joined together along the left and right and bottom edges while the top edge remains unbounded to access an interior region of the receptacle. A flap extends from the rear panel adjacent the top edge of the receptacle. A portion of the flap adjacent the top edge of the receptacle comprises a hinge. A connector is operatively disposed between the flap and the front panel of the receptacle for releasably securing the flap to the receptacle in an overlapping relationship to enclose the unbounded top edge of the receptacle. An improvement of this invention is found in a jam cleat that is disposed along at least one of the left and right edges adjacent the top edge of the receptacle. The jam cleat forms a breach in the pocket that is configured to receive the loose portion of the medical tube. The jam cleat is a passive feature that automatically applies a progressive wedge force on the medical tube in response to a tensile force along the medical tube.

According to a second aspect of this invention, a combination medical tube and securing pocket is provided. The combination includes a medical tube that has a loose portion and an implanted portion. The loose portion has a coiled section and a tethered section. The implanted portion is adapted to be attached directly to the body of a patient. A receptacle is formed between a flexible front panel and a flexible rear panel. The coiled section of the medical tube is disposed within the receptacle. The receptacle has left and right and top and bottom edges. The front and rear panels are joined together along the left and right and bottom edges while the top edge remains unbounded to enable access to an interior region of the receptacle. A flap extends from the rear panel adjacent the top edge of the receptacle. A portion of the flap that is adjacent the top edge of the receptacle comprises a hinge. A connector is operatively disposed between the flap and the front panel of the receptacle for releasably securing the flap to the receptacle in an overlapping relationship to enclose the coiled section of the medical tube in the receptacle. A jam cleat is located along at least one of the left and right edges adjacent the top edge of the receptacle. The jam cleat forms a breach in the receptacle through which the tethered section of the medical tube extends. The jam cleat is configured to apply a progressive wedge force on the medical tube in response to a tensile force along the medical tube.

The jam cleat interacts with the loose portion of the medical tube to generate a self-arresting braking force on the medical tubing that is generally proportional to the amount of tension applied. Greater tensile force will have the effect of more aggressively drawing the tube into the jam cleat. The jam cleat is bi-directional, in that a hazardous tensile force directed either inwardly or outwardly from the receptacle will be progressively arrested regardless of which part of the loose portion experiences an unexpected tugging. The harder the medical tube is pulled, the deeper the transiting segment of the loose portion is pulled into the jam cleat progressively increasing the friction and resisting movement. For the patient, this progressive arresting reaction force generated by the jam cleat will be felt as a reaction force along the implanted portion. The patient will sense a reaction force through their skin. Even for infant patients, the intuitive reaction will be to take remedial action—usually to reduce the sensed pulling by moving into the direction of the tugging force. However, because the jam cleat allows some degree of slippage, there is a cushioning effect in that slower patient reaction times are not met with a harsh response. Instead, the automatic braking effects of the jam cleat generously gives the patient (or a supervising caregiver) some time and opportunity to recognize the problem and take corrective action. Thus, the novel securing pocket of this invention reduces the incidence of skin tears from tape due to accidental removal and helps to reduce the incidence of an implanted portion 10 being accidentally removed.

BRIEF DESCRIPTION OF THE SEVERAL VIEWS OF THE DRAWINGS

These and other features and advantages of the present invention will become more readily appreciated when considered in connection with the following detailed description and appended drawings, wherein.

DETAILED DESCRIPTION OF THE INVENTION

Figure 1:
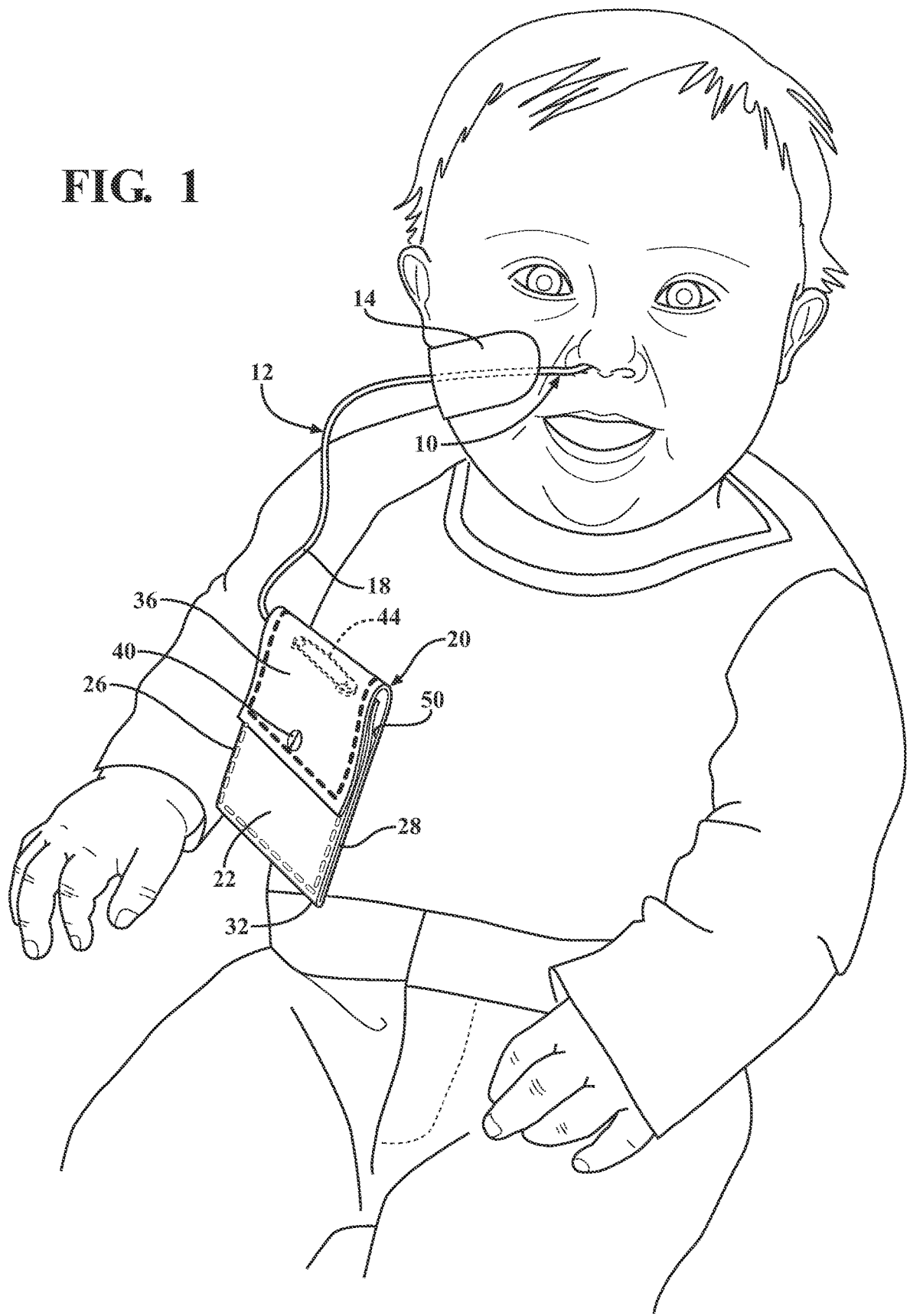
FIG. 1 shows a human patient fitted with a medical tube in the form of a nasogastric feeding tube, and having affixed to her shirt a securing pocket according to one embodiment of this invention in which a loose portion of the medical tube is stored.

Referring to the figures, wherein like numerals indicate like or corresponding parts throughout the several views, a medical tube is shown having an implanted portion 10 (FIG. 1 only) and a loose portion 12. For most applications, medical tubing is made from a wide range of flexible materials including urethanes, polyvinylchlorides, silicone rubber, polytetrafluoroethylenes and latex to name a few. Typically, medical tubing as used in connection with this present invention will have an outer diameter $D_T$ (FIGS. 6 and 7) in the range of about 0.3 mm to about 5 mm. Thus, the medical tube according to this invention can be any such tube of medical grade that has an implanted portion 10 securely affixed to (and usually partially penetrating) the body of the patient, and an opposite loose portion 12 that is intermittently disconnected from a medical device such as a drip bag or feed bag or syringe, etc.

The implanted portion 10 includes the length of tube inside the patient's body as well as any exposed sections that are affixed directly to the patient such as by adhesive tape 14. When the loose portion 12 is disconnected from its medical device, it must be managed to avoid inadvertent snagging and meddling. Snags and meddling risk pulling at the adhesive tapes 14 and potentially withdrawing the implanted portion 10 from its ideally placed position in the patient. According to the principles of this invention, proper management of the loose portion 12 including winding the distal end of the loose portion 12 into a neat coil. Any length of the loose portion 12 that remains not coiled serves as a tether to the implanted portion 10. Thus, the loose portion 12 is composed of a coiled section 16 and a tethered section 18. The tethered section 18 is located between the coiled section 16 and the implanted portion 10. The relative lengths of the coiled 16 and tethered 18 sections are formed on a case-by-case basis, instinctively, by the attending caregiver or by the patient each time the loose portion 12 is disconnected from its associated medical device (not shown) and coiled for management purposes. Ideally, the tethered section 18 is significantly shorter in length than the coiled section 16.

For convenience, the following descriptions will make reference to medical grade tubes configured for use as Nasogastric and Nasojejunal (NG/NJ) tubes. The implanted portion 10 of NG/NJ tubes are inserted intranasally, as shown in FIG. 1. However, NG/NJ tubes are not the only types of medical tubes with which the concepts of this invention may be applied. Other examples of medical tubes include, but are not limited to, those used in connection with intravenous therapy and catheters, to name a few.

A securing pocket according to one exemplary embodiment is generally shown at 20. The securing pocket 20 is provided for safely and effectively managing the entire loose portion 12 of the medical tube while the implanted portion 10 remains attached to the patient's body. The securing pocket 20 has a receptacle that encloses the coiled section 16 of the loose portion 12 in a neat winding to avoid the possibility for snagging, meddling or unwanted residual drainage while concurrently controlling the tethered section 18 so that it is less likely to pull adversely on the implanted portion 10. Thus, the securing pocket 20 reduces the risk that an accidental snag will occur, or that the loose portion 12 of medical tube will attract unwanted meddling (such as from the curiosity of an infant patient).

The receptacle feature of the securing pocket 20 is formed between a flexible front panel 22 and a flexible rear panel 24. The coiled section 16 of the loose portion 12 of the medical tube is disposed within the receptacle when not otherwise in service connected to a medical device. The receptacle has left 26 and right 28 and top 30 and bottom 32 edges. The front 22 and rear 24 panels are joined together along the left 26 and right 28 and bottom 32 edges with stitching 34 or adhesive or welding or other suitable fastening methods. The top edge 30 of the receptacle remains unbounded to enable access to the interior region of the receptacle. That is to say, the front 22 and rear 24 panels are separable along the top edge 30 like a mouth for loading and unloading the coiled section 16 of the medical tube.

In the illustrated examples of FIGS. 1-6, the left 26 and right 28 edges are straight and parallel to one another along their entire lengths. As shown in the alternative embodiment of FIG. 7, this is not a requirement of the invention. Nevertheless, there is some advantage to configuring the left 26 and right 28 edges so that each has at least a straight segment adjoining the top edge 30. Likewise, the bottom edge 32 appears straight along its entire length in the embodiment of FIGS. 1-6. However, this also is shown not to be a requirement of the invention via the alternative embodiment of FIG. 7.

Figure 4:
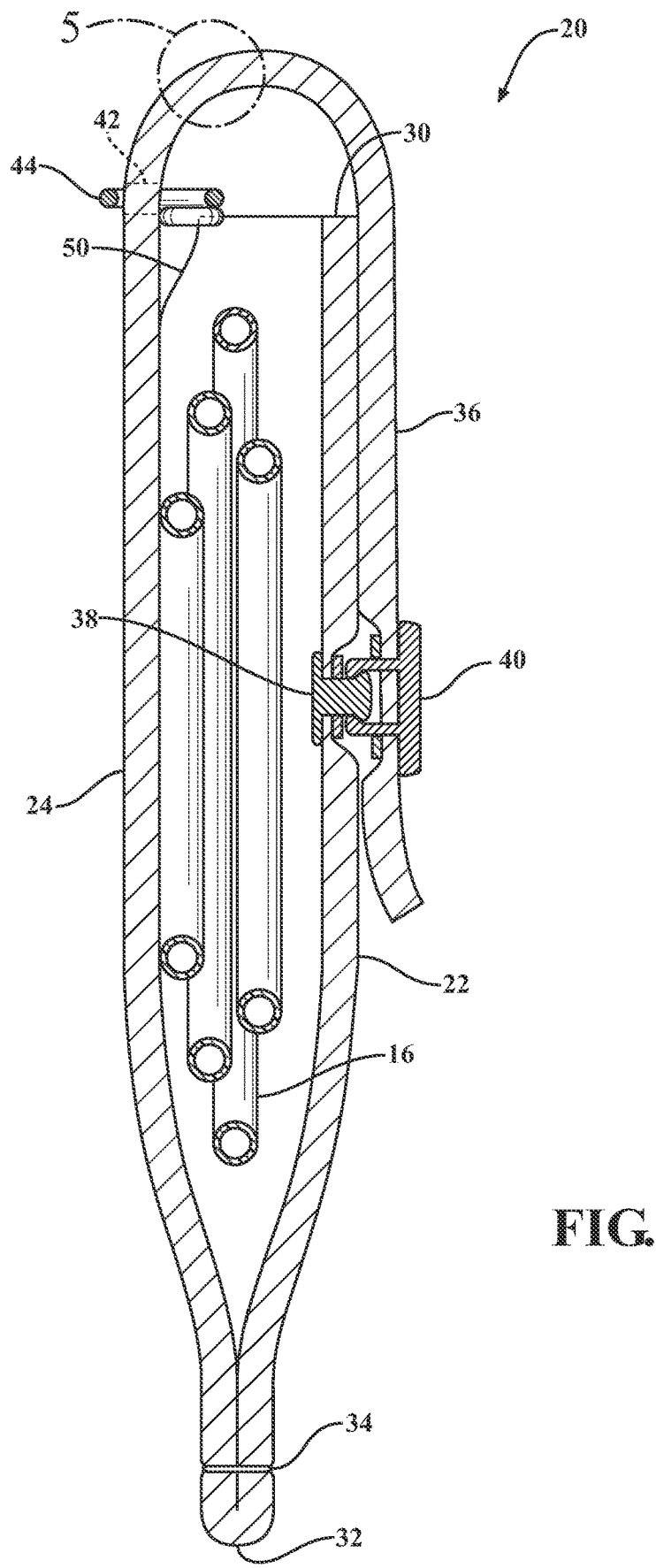
FIG. 4 is a cross-section view taken generally along lines 4-4 in FIG. 2.

A flap 36 extends from the rear panel 24 adjacent the top edge 30 of the receptacle. A portion of the flap 36 adjacent the top edge 30 of the receptacle comprises an integral, i.e., living, hinge. This is perhaps best seen in FIG. 4. A connector is operatively disposed between the flap 36 and the front panel 22 of the securing pocket 20 for releasably securing the flap 36 in an overlapping relationship. The connector can take many different forms, each typically comprising a first part 38 and a mating second part 40. The first part 38 is fixedly attached to the inside of the flap 36 and the second part 40 is fixedly attached to the front panel 22 exterior. These hold the receptacle shut once the coiled section 16 of a medical tube has been inserted into the receptacle. In the illustrated examples, the connector is shown in the form of a snap device, wherein one of the first and second parts 38, 40 is a male side and the other of the first and second parts 38, 40 is a female side. When the first 38 and second 40 parts are aligned and pressed together, they will self-lock to secure the flap 36 in a closed condition (FIG. 4). Naturally, many alternative options are available for the connector, including such devices as hook-and-loop, magnets, buttons, safety pins, straight pins, clips, drawstring, adhesive tape, and the like. To be clear, materials suitable for use as a connector include, but are not limited to, snaps or hooks made of any substance (i.e. plastic, metal, rubber, and the like), any type/size of hook-and-loop (e.g., Velcro®), any type/size of safety pin or straight pin, any type/size of rubber band, any type/size of zipper, any type/size of clip and/or buckle (metal, plastic, and the like), any sticky/adhesive/tape substance (be it a peel and stick attachment and the like), any type/size of button, any type/size of string or rope or drawstring made of any kind of substance or composite, any combination of the aforementioned materials. All materials listed, whether industrial and medical grade or non-industrial or non-medical grade or the composites of said materials will also be included. Furthermore, the closure could also be some form of self-closing hinge feature or a weighted flap 36 that biases the flap 36 toward an always-closed condition. Although the preferred embodiments of this invention include some form of connector, it is contemplated that the invention may be practiced without any closure whatsoever, leaving a flap 36 that does not secure closed.

At least one eyelet 42 is formed along the hinge, preferably at or directly adjacent to the top edge 30. In the illustrated embodiments, the eyelet 42 comprises first and second pin eyelets 42, each reinforced around the edges such as with a common button-hole stitch. An anchoring device is operatively disposed through the eyelet 42 to support the securing pocket 20 on an article of clothing worn by the patient. Advantageously, the anchoring device allows the securing pocket 20 to be worn in a variety of ways, including attached to clothing, to a lanyard or necklace, to a hat, to a headband, to a wrist or arm band, or even attached directly to skin via tape or other suitable adhesive substances.

Figure 3:
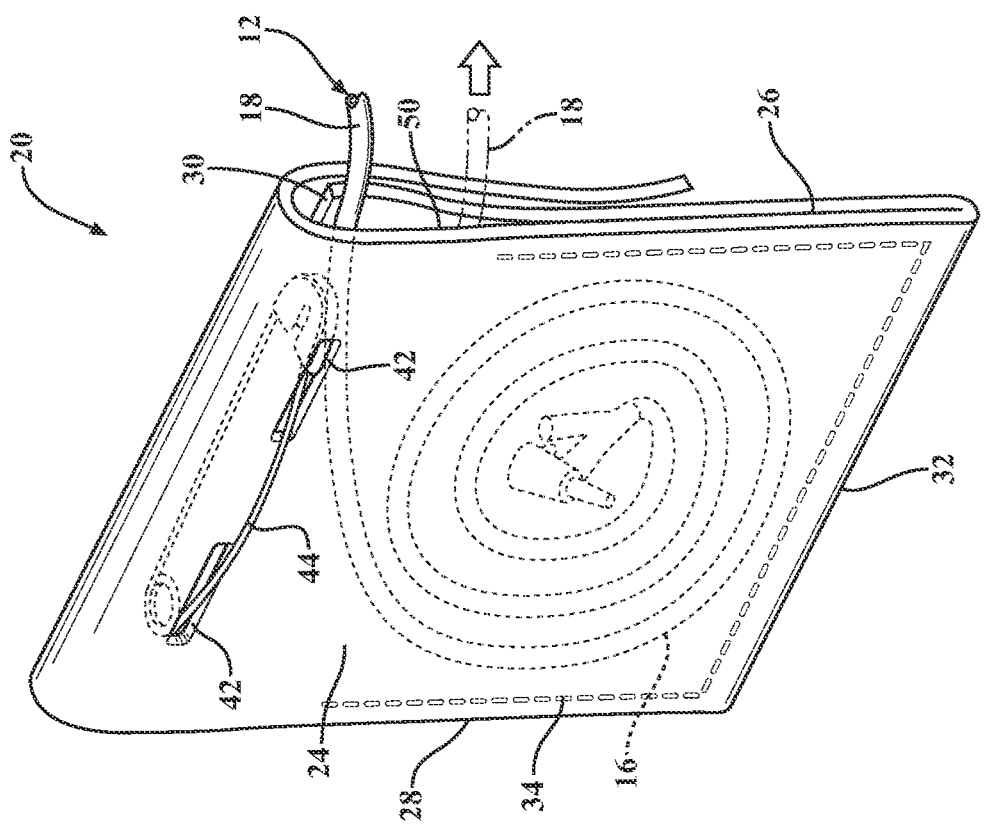
FIG. 3 is a rear perspective view of the securing pocket of FIG. 1 again showing the tethered section of the feeding tube extending through the jam cleat and automatically wedging itself in response to tensile force applied to the medical tube.
Figure 2:
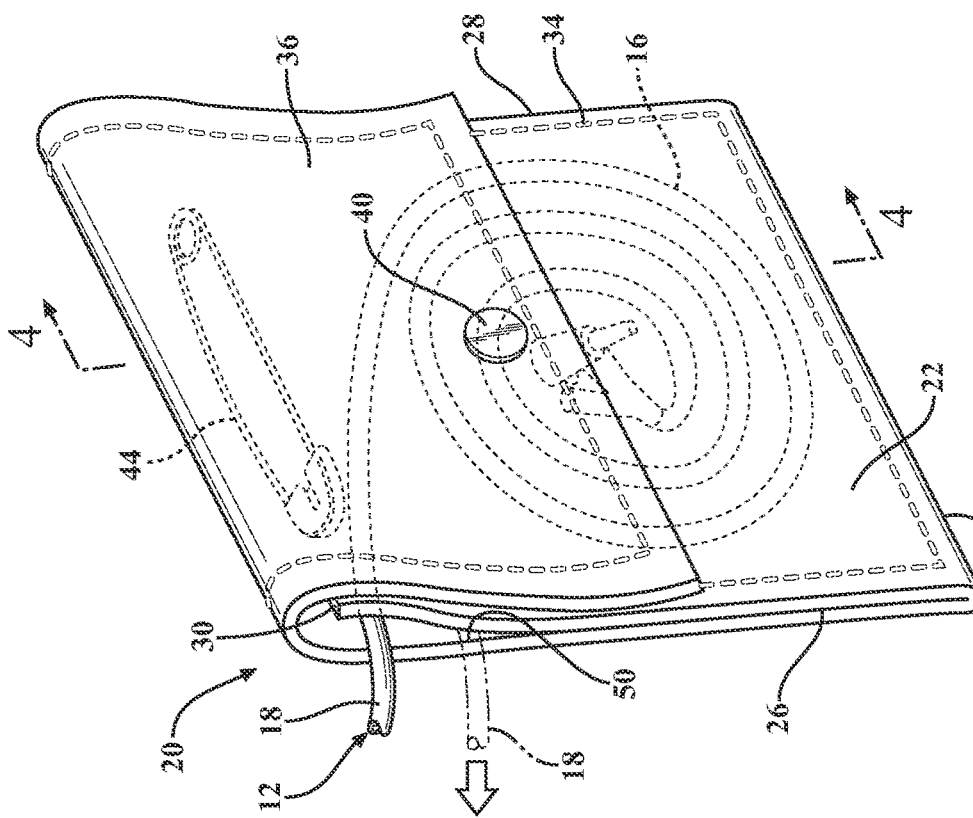
FIG. 2 is a front perspective view of the securing pocket of FIG. 1 depicting the loose portion of the medical tube in hidden lines, and further showing a tethered section of the feeding tube self-arresting in a jam cleat in response to a tensile force applied to an implanted portion of the medical tube.
Figure 6:
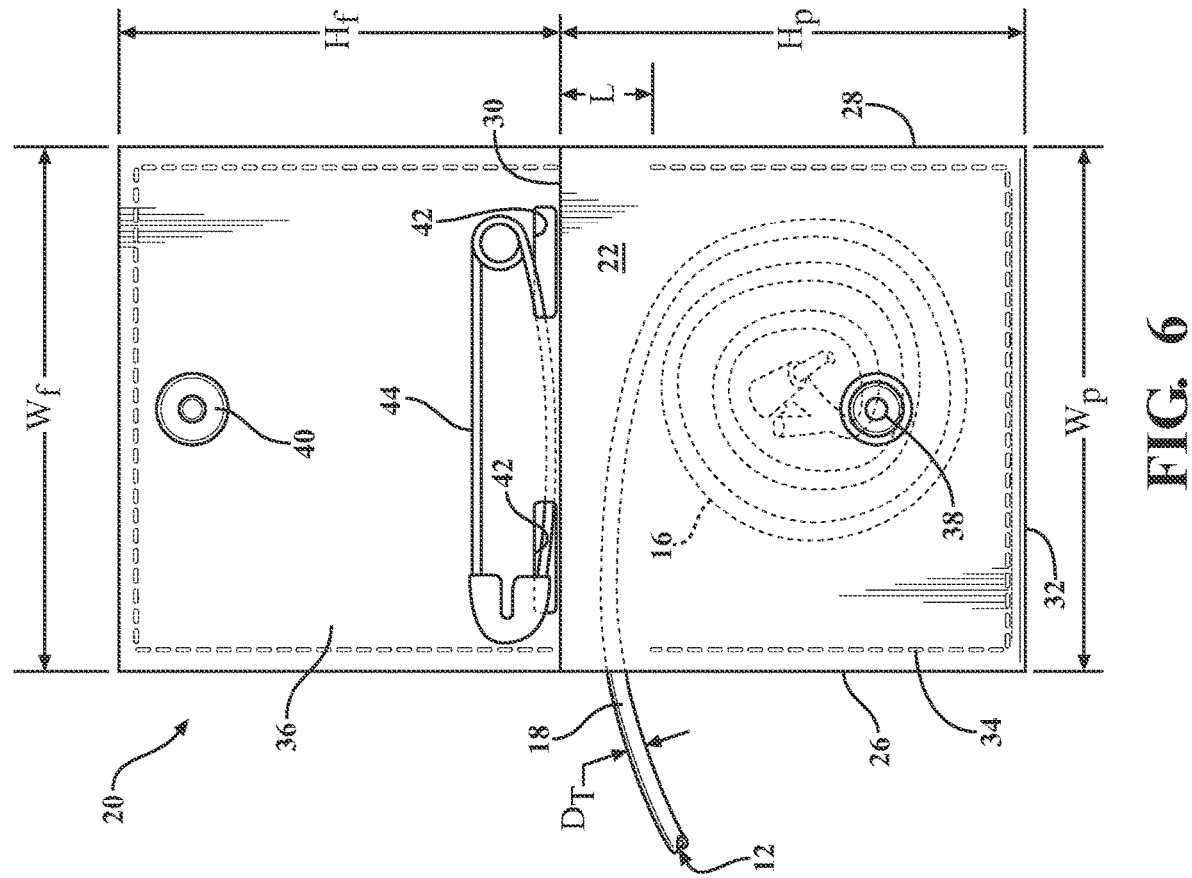
FIG. 6 is a front elevation of the securing pocket of FIG. 1 but showing the flap in a raised position as when loading/unloading the loose portion of the medical tube in the receptacle or attaching the securing pocket to a patient with the provided safety pin.

The anchoring device may be any suitable device, including but not limited to a standard safety pin 44 having its pointed shaft threading through the respective eyelets 42 as shown in FIGS. 3 and 6. In this configuration, the spaced-apart eyelets 42 allow the safety pin 44 to attach the securing pocket 20 to clothing. Important in this feature is the fact that the wearer does not need to repeatedly pierce the fabric and inner lining of the receptacle with the safety pin each time it is worn, otherwise causing the fabric to fray and eventually tear. The location of the eyelets 42 also ensure the wearer places the safety pin in the correct location of the receptacle for attachment purposes and maximum effectiveness of the product. Finally, the location of the eyelets 42 keep the head of the safety pin 44 hidden and inaccessible under the flap 36 when the receptacle is closed. This resists children from accessing the safety pin 44 and opening it, possibly removing the securing pocket 20 or injuring themselves. To be clear, the anchoring device may alternatively be fashioned from any of various suitable forms including, but not limited to, safety pins/straight pins of any type/size, clips of any type/size or shape (be they plastic, metal, rubber, and the like), buttons of any type/size, hook-and-loop (e.g., Velcro®) of any type/size, string or drawstring or rope of any type/size and made of any kind of substance or composite, any sticky/adhesive/tape substance (be it a peel and stick attachment and the like), the securing pocket 20 being worn in ways other than attached to clothing (i.e. as a necklace, as part of a hat, as part of a headband, as part of a wrist or arm band, attached directly to skin via tape or other adhesive substances). All materials listed, whether industrial and medical grade or non-industrial or non-medical grade or the composites of said materials will also be included. Also contemplated is the omission of any type of anchoring device leaving a securing pocket 20 that does not attach to the patient or his/her clothing or accessories.

The flap 36, therefore, helps secure the coiled section 16 of medical tube from sliding out of the receptacle when the snap is shut. The flap 36 also prevents young children from accessing the safety pin 44 that attaches the securing pocket 20 to clothing or withdrawing the coiled section 16 from the receptacle which might result in fluid leakage and/or pulling against the implanted portion 10 of the medical tube. To say again, the safety pin 44 is only accessible when the flap 36 is open. At all other times, the safety pin 44 is sheathed and kept secure from the fingers of curious children. In addition, another subtle but important advantage of using a safety pin 44 as the anchoring device is that attachment at two spaced points on the clothing (i.e., where the pointed pin shaft enters and exits the clothing) aids in keeping the securing pocket 20 close to the patient's body and out of sight to an extent. This is important for applications involving infants and very young children (FIG. 1) who would be naturally curious to play with the securing pocket 20 when in their field of view, but content to ignore the securing pocket 20 when outside their field of view.

Turning now to FIG. 6, various dimensional attributes of the securing pocket 20 are shown. Most if not all of these dimensional attributes contribute to the overall effectiveness of the securing pocket 20. For example, the distance between the left 26 and right 28 edges comprises a pocket width $W_p$. The distance between the bottom 32 and top 30 edges comprises a pocket height $H_p$. The pocket width $W_p$ is generally equal to the pocket height $H_p$. In the example of FIG. 6, this results in a generally square-shaped receptacle. In the alternative example of FIG. 7, this result in a U-shape. Other geometric configurations are likely possible.

A benefit of maintaining the pocket width $W_p$ generally equal to the pocket height $H_p$ is that the coiled section 16 of tube will always naturally expand to assume the shape of its container. A receptacle having generally equal width and height will allow the coiled section 16 to naturally expand into a nearly circular shape, which is most efficient to avoid tangles and generally equalizes the bending stresses throughout the coiled section 16. In addition, the generally equal pocket width $W_p$ and pocket height $H_p$ allows the coiled section 16 of tube to be inserted in either a right-handed (FIG. 6) or left-handed (FIG. 7) wound direction, the advantages of which will be described below. The flap 36, in turn, has a flap height $H_f$ between approximately one-third and one times the pocket height $H_p$. The flap 36 has a flap width $W_f$ that is generally equal to the pocket width $W_p$. In this manner, the flap 36 will effectively close the mouth of the receptacle and also protectively sheath the safety pin 44.

Figure 5:
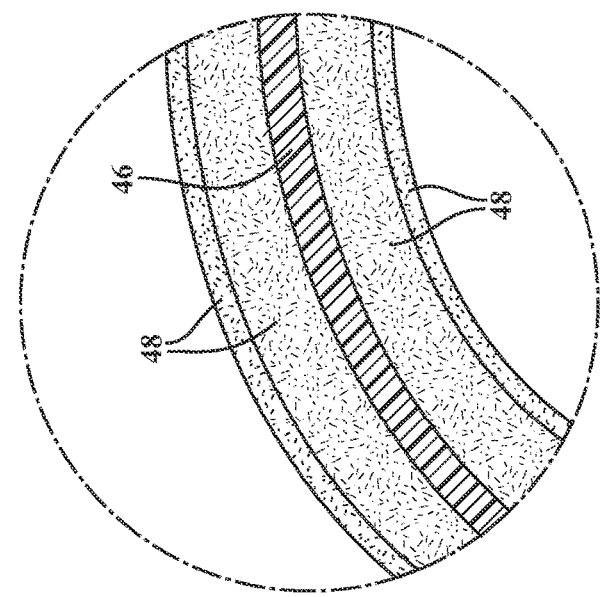
FIG. 5 is an enlarged view of the region circumscribed at 5 in FIG. 4.

In terms of materials, the securing pocket 20 (receptacle and flap 36) can be fabricated from a wide variety of available materials, many of which are expressly mentioned in the following paragraphs. However, the illustrated examples depict a securing pocket 20 fabricated primarily from a multi-layer fabric material. FIG. 5 portrays a magnified cross-section of the multi-layer fabric material. At the center is an optional water-impermeable core 46. The term "water-impermeable" is intended to include all forms of resistant and repellant designs, even if some permeability exists in reality. This water-impermeable core may be made of any suitable material, including but not limited to a vinyl-based composition. The water-impermeable core 46 aides in catching drips that may come from the access port end of the coiled section 16 when it leaks. Located within the entire boundaries of the receptacle, this water-impermeable core 46 also creates a thicker, more durable and stationary feel to the securing pocket 20. It is this water-impermeable core 46 that helps to prevent the receptacle from wrinkling along the safety pin 44 when worn, and helps to maintain the receptacle shape when the coiled section 16 is inserted. This water-impermeable core 46 also serves as a barrier to excessive pulling on the snaps 38/40 and eyelets 42 while the securing pocket 20 is being worn, preserving the service life of the securing pocket 20.

The water-impermeable core 46 separates exterior layers 48 which may be of any suitable type. As shown here in FIG. 5, the exterior layers 48 may be cotton-based materials. One or both of the exterior layers 48 can themselves be a double layer of fabric to aid in catching and absorbing drips that may come from the access port end of the medical tube. Cotton is an ideal choice as it is washable and allows the wearer to use the securing pocket 20 for a length of time, wash and dry it, and reuse it often. The fabric layers 48 also serve as a way for the wearer to express his or her personal style by choosing different patterns and designs. That is, the exterior layers 48 can serve as an artistic canvas that allows the wearer to express their personal style.

The aforementioned materials are offered as examples only, and it will be understood that many alternatives for the exterior layers 48 are contemplated and available. Alternatives include, but are not limited to, foams, all types of paper, woven materials (i.e. ballistic, circular knit, and the like), non-woven fabrics, thermal fabrics of any kind, any type of batting or filling (be it organic, polyester, or the like), natural fibers, mesh, woven fabric (i.e. cotton, flannel, gunny cloth, hessian, and the like), silicone, rubber, latex, plastics (both hard and soft such as vinyl, polymer, thermoplastic polyurethane (TPU) film, and the like), GORE-TEX®, Kevlar® and any type of metal. Also included are any other absorbent, sheet-like materials that are flexible in nature. All materials listed, whether industrial and medical grade or non-industrial or non-medical grade or the composites of said materials are also contemplated.

Likewise, many alternative materials used for the interior core 46 are also contemplated and include foam, woven materials (i.e. ballistic, circular knit, and the like), non-woven fabrics, thermal fabrics of any kind, natural fibers, mesh, woven fabric (i.e. cotton, flannel, gunny cloth, hessian, and the like), silicone, rubber, latex, any type of batting or filling (be it organic, polyester, or the like), plastics (both hard and soft such as vinyl, polymer, thermoplastic polyurethane (TPU) film, and the like), GORE-TEX®, Kevlar® and any type of metal. Also included are any other non-absorbent, sheet-like materials that are flexible in nature. All materials listed, whether industrial and medical grade or non-industrial or non-medical grade or the composites of said materials are contemplated. Also contemplated is a composition devoid of the core lining 46, leaving only the outer structure 48.

Another significant feature of this invention is the inclusion of a jam cleat 50 disposed along at least one of the left 26 and right 28 edges of the receptacle adjacent the top edge 30. Preferably, but not necessarily, one jam cleat 50 is disposed along each of the left 26 and right 28 edges adjacent the top edge 30 of the receptacle. In this manner, the securing pocket 20 is provided with two jam cleats 50, one enabling tube egress via the left edge 26 and another enabling tube egress via the right edge 28. Perhaps best shown in FIGS. 2 and 3, the jam cleat 50 forms a breach, or gap or opening, in the receptacle through which the loose portion 12 of the medical tube transitions between its coiled 16 and tethered 18 sections. It could be said that the tethered section 18 of the medical tube is operatively disposed in the jam cleat 50, just upstream of the coiled section 16. The aforementioned straight segments along the tops of the left 26 and right 28 edges are unstitched so as to define the breach between the front 22 and rear 24 panels through which a short length of the loose portion 12 of the medical tube may pass.

Figure 7:
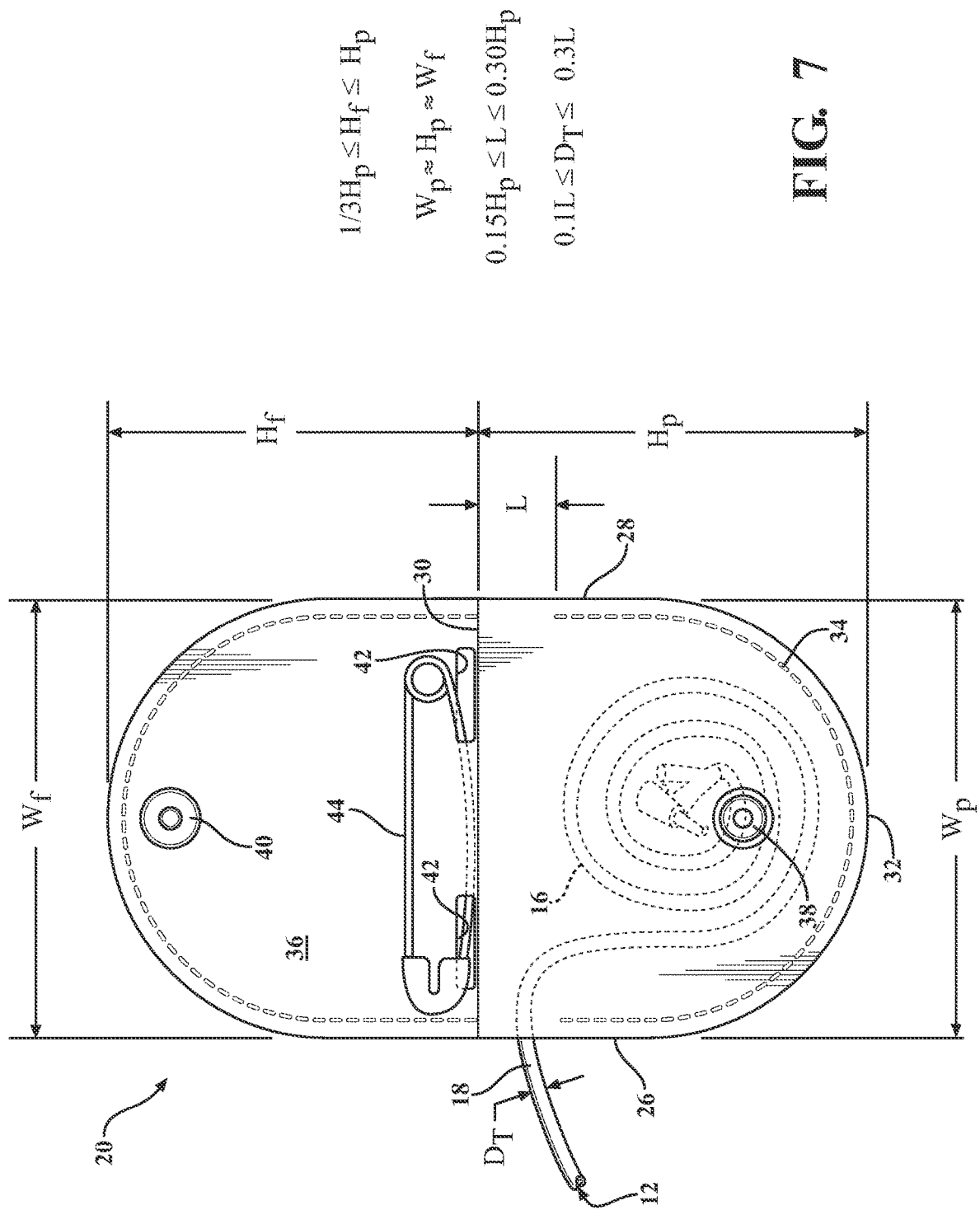
FIG. 7 is a front elevation of an alternative embodiment of the securing pocket with dimensional call-outs for various features.

Each jam cleat 50 comprises a V-shaped notch integrally formed at the intersection of the front 22 and rear 24 panels. The location of the jam cleat 50 adjacent the top edge 30 of the receptacle makes loading the coiled section 16 easier because there is not any need to thread the loose portion 12 through a slit as is required in some of the prior art examples mentioned above. Instead, a piece of the tethered section 18 naturally falls into the jam cleat 50 when the coiled section 16 is placed into the receptacle. And conversely, the tethered section 18 naturally and effortlessly lifts out of the jam cleat 50 when the coiled section 16 is removed from the receptacle. Furthermore, the location of the jam cleat 50 adjacent the top edge 30 of the receptacle assures that the tethered section 18 will be pulls down into the V whenever tugged. The coiled section 16 inside the receptacle is almost if not entirely at rest below the top edge 30. Whenever the exposed tethered section 18 is pulled, as by an inadvertent snag or meddling (in the case of a curious child), the medical tubing will attempt to unwind from its coil which will have the effect of drawing the tethered section 18 down into the jam cleat 50. By reversing the direction of coil as shown in FIG. 7, the tethered section 18 will be more aggressively pulled down into the V. The generally equal pocket width $W_p$ and pocket height $H_p$ allows the coiled section 16 of tube to be inserted in either a right-handed (FIG. 6) or left-handed (FIG. 7) wound direction. When combined with jam cleats 50 on each of the left 26 and right 28 sides, the user can choose between a more-aggressive or less-aggressive braking action depending on the circumstances. Because the front 22 and rear 24 panels are flexible, the jam cleat 50 is naturally formed with soft and flexible sides as well. This makes the shape of the jam cleat 50 somewhat dynamic, and particularly distinct from examples of jam cleats 50 found in general rigging and marine applications. Thus, the V-shape of the jam cleat 50 may be characterized as having moveable or yieldable sides, which in turn make it ideally adapted for the medical application of managing the loose portion 12 of a medical tube.

All of these features of the jam cleat 50 work together, in varying degrees, to apply a progressive wedge force on the tethered section 18 in response to a hazardous tensile force along the medical tube. Hazardous tensile forces occur either when the exposed tethered section 18 is unexpectedly yanked, or when the securing pocket itself (including the clothing to which it may be anchored) is pulled away from the implanted portion 10. In both these situations, if the loose portion 12 of the medical tube is not properly managed, a sharp pull will be applied to the implanted portion 10 which could cause injury to site of adhesive tape 14 and/or dislodging of the implanted portion 10 inside the patient's body.

The jam cleats 50 create exclusive breaches in the receptacle (when flap 36 is closed) where the coiled section 16 and tether section 18 meet. That is, the jam cleats 50 interact with the loose portion 12 at a mid-length transition region in-between its coiled 16 and tethered 18 sections. This mid-span location along the loose portion 12 allows the jam cleats 50 to work in either direction—meaning a hazardous tensile force that is directed inwardly or outwardly from the receptacle regardless of which part of the loose portion 12 experiences an unexpected tugging. While the receptacle is open, the flap 36 provides ease to place the coiled section 16 of the tube in the correct location within the receptacle. But when the flap 36 is snapped shut, a transiting segment of the loose portion 12 is saddled in a jam cleat 50 so that slide in or out only with resistance. The harder the medical tube is pulled, the deeper the transiting segment of the loose portion 12 is pulled into the V like a wedge progressively increasing the friction and resisting movement. That is to say, the jam cleats 50 generate a self-arresting braking force on the medical tubing that is generally proportional to the amount of tension applied. Greater tensile force will more aggressively attempt to unwind the coiled section 16, which will have the effect of more aggressively drawing the tethered section 18 down into the jam cleat 50.

For the patient, this progressive arresting reaction force generated by the jam cleats 50 will be felt as a reaction force along the implanted portion 10. In cases where tape 14 is used to secure the implanted portion 10 of the medical tube, the patient will sense the reaction force through their skin.

Even for infant patients, the intuitive reaction will typically be to take remedial action—usually to reduce the sensed pulling by moving into the direction of the tugging force. However, because the jam cleats 50 allow some degree of slippage, there is a cushioning effect in that slower patient reaction times are not met with a harsh response. Instead, the automatic braking effects of the jam cleat 50, located midspan of the loose portion 12, generously gives the patient (or a supervising caregiver) some time and opportunity to recognize the problem and take corrective action.

These benefits are favorably compounded by the flexible sides of the jam cleats 50. Hazardous tensile forces cannot be expected to always arise in the plane of the receptacle. Rather, it is foreseeable that the loose portion 12 could be snagged and tugged from many oblique vectors which will cause the segment of the tube transiting the jam cleat 50 to bear with pressure against either the front 22 or rear 24 panel. The flexible nature of these panels 22, 24 will cause the jam cleat 50 to gently spread apart while still urging the tube toward the V bottom. Accordingly, should a patient turn their head quickly, catch their tube on something, or somehow snag the tube, the jam cleats 50 allow the loose portion 12 to slide, sometimes by 1 to 2 inches, with accompanying resistance. This grace period allows the patient or caregiver some time to assess the situation and take corrected steps (if even reflexively). The end effect is that a small snag or inadvertent pulling on the loose portion 12 is substantially less likely to cause a sharp pull on the tape 14 which could lead to tearing of the skin and/or dislocation of the implanted portion 10 of the tube. The jam cleat 50 is preferably placed on both sides of the receptacle so the wearer is not limited to wearing the securing pocket 20 on one side of their body but may comfortably attach the securing pocket 20 on either side of his/her person.

The length L of each jam cleat 50 is between about 0.15 and 0.30 times the pocket height $H_p$. Thus, in an example where the pocket height $H_p$ is 2.75 inches, the length L of each jam cleat 50 will be between about 0.4 and 0.8 inches. If the length L of the jam cleat 50 is significantly shorter than this range, too much resistance friction will be generated and there will not be sufficient sliding length. On the other hand, if the length L of the jam cleat 50 is significantly greater than this range, too little frictional resistance will be generated and there will be much sliding length in the event of an inadvertent pulling on the loose portion 12.

The foregoing invention has been described in accordance with the relevant legal standards, thus the description is exemplary rather than limiting in nature. Variations and modifications to the disclosed embodiment may become apparent to those skilled in the art and fall within the scope of the invention. For example, alternate contemplated design features include changes in the overall pocket design. These may include changes in: shape (be it slight or large variations in length or height, large changes such as circles, triangles, a-symmetrical shapes, and the like); location of parts (i.e. moving the flaps, the snaps, the eyelets, the safety pin, the interior lining); removal of parts (i.e. excluding the flaps, the snaps, the eyelets, the safety pin, the interior lining); changing the number of parts (different number of snaps, safety pins, layers of materials used, eyelets, flaps); changing structure of the Pocket including creating a larger/smaller pocket to flap ratio, moving the snap or equivalent to the back of the pocket and having the pocket snap shut through any type of opening (be it hole or slit or large cutout) in the interior panel of the receptacle, having the receptacle open on more than one side, changing the intent of the securing pocket 20 to include any other types of medical tubing/products/equipment. Additions to the pocket are included as well. These could be alterations such as inclusion of a second receptacle, a divider in the receptacle, added materials to the jam cleat 50 to aid in further resistance, an interior part made of any substance that the tube wraps around (may be attached or unattached to the pocket), or any other additional alterations.

What is claimed is:

1. A securing pocket for managing a loose portion of a medical tube while an implanted portion of the medical tube remains attached to the patient's body, said securing pocket comprising:
    a receptacle formed between a flexible front panel and a flexible rear panel, said receptacle having left and right and top and bottom edges, said front and rear panels being joined together along said left and right and bottom edges while said top edge remains unbounded to access an interior region of said receptacle,
    a flap extending from said rear panel adjacent said top edge of said receptacle, a portion of said flap adjacent said top edge of said receptacle comprising a hinge, and
    a jam cleat disposed along at least one of said left and right edges adjacent said top edge of said receptacle, said jam cleat forming a breach in said receptacle configured to receive a tethered section of the medical tube and apply a progressive wedge force on the medical tube in response to a tensile force along the medical tube.

2. The securing pocket of claim 1 wherein one said jam cleat is disposed along each of said left and right edges adjacent said top edge of said receptacle.

3. The securing pocket of claim 1 wherein said jam cleat comprises a V-shaped notch integrally formed at the intersection of said front and rear panels.

4. The securing pocket of claim 3 wherein said left and right edges each have a straight segment adjoining said top edge, the distance between said left and right edges comprising a pocket width ($W_p$), the distance between said bottom and top edges comprising a pocket height ($H_p$), said pocket width ($W_p$) being generally equal to said pocket height ($H_p$).

5. The securing pocket of claim 4 wherein one said jam cleat is disposed along each of said left and right edges adjacent said top edge of said receptacle, the one said jam cleat is disposed in each of said straight segments of said left and right edges.

6. The securing pocket of claim 5 wherein each said jam cleat has a length (L) that is between about 0.15 and 0.30 times said pocket height ($H_p$).

7. The securing pocket of claim 1 wherein said flap includes at least one eyelet formed along said hinge, an anchoring device operatively disposed through said eyelet.

8. The securing pocket of claim 7 wherein said anchoring device comprises a safety pin.

9. The securing pocket of claim 1 wherein the distance between said left and right edges comprises a pocket width ($W_p$), the distance between said bottom and top edges comprises a pocket height ($H_p$), said pocket width ($W_p$) being generally equal to said pocket height ($H_p$), said flap having a flap width ($W_f$) generally equal to said pocket width ($W_p$), said flap having a flap height ($H_f$) that is between about 0.3 and 1.0 times said pocket height ($H_p$).

10. The securing pocket of claim 1 further including a connector operatively disposed between said flap and said front panel of said receptacle for releasably securing said flap to said receptacle in an overlapping relationship to enclose said unbounded top edge of said receptacle, said connector comprising a first part and a mating second part, said first part fixedly attached to said flap and said second part fixedly attached to said front panel of said receptacle.

11. The securing pocket of claim 1 wherein said receptacle and said flap each being fabricated from a multi-layer fabric material, said multi-layer fabric material having a water-impermeable core.

12. The securing pocket of claim 11 wherein said water-impermeable core comprises vinyl, said multi-layer fabric material having cotton-based external layers.

13. A combination medical tube and securing pocket comprising:
  a medical tube having a loose portion and an implanted portion, said implanted portion adapted to be attached to the body of a patient, said loose portion having a coiled section and a tethered section,
  a receptacle formed between a flexible front panel and a flexible rear panel, said coiled section of said medical tube disposed within said receptacle, said receptacle having left and right and top and bottom edges, said front and rear panels being joined together along said left and right and bottom edges while said top edge remains unbounded to access an interior region of said receptacle,
  a flap extending from said rear panel adjacent said top edge of said receptacle, a portion of said flap adjacent said top edge of said receptacle comprising a hinge, and
  a jam cleat disposed along at least one of said left and right edges adjacent said top edge of said receptacle, said jam cleat forming a breach in said receptacle, said tethered section of said medical tube operatively extending through said jam cleat, said jam cleat configured to apply a progressive wedge force on said tethered section of said medical tube in response to a tensile force along said medical tube.

14. The combination of claim 13 wherein one said jam cleat is disposed along each of said left and right edges adjacent said top edge of said receptacle.

15. The combination of claim 13 wherein said jam cleat comprises a V-shaped notch integrally formed at the intersection of said front and rear panels.

16. The combination of claim 13 wherein said tethered section of said medical tube has a diameter ($D_T$), said jam cleat having a length (L) that is between about 4 and 8 times said medical tube diameter ($D_T$).

17. The combination of claim 13 further including a connector operatively disposed between said flap and said front panel of said receptacle for releasably securing said flap to said receptacle in an overlapping relationship to enclose said coiled section of said medical tube in said receptacle, and wherein said flap includes at least one eyelet formed along said hinge, a safety pin operatively disposed through said eyelet.

18. The combination of claim 13 wherein the distance between said left and right edges comprises a pocket width ($W_p$), the distance between said bottom and top edges comprises a pocket height ($H_p$), said pocket width ($W_p$) being generally equal to said pocket height ($H_p$), said flap having a flap width ($W_f$) generally equal to said pocket width ($W_p$), said flap having a flap height ($H_f$) that is between about 0.3 and 1.0 times said pocket height ($H_p$).

19. The combination of claim 13 wherein said receptacle and said flap each being fabricated from a multi-layer fabric material, said multi-layer fabric material having a water-impermeable core.

20. A securing pocket for managing a loose portion of a medical tube while an implanted portion of the medical tube remains attached to the patient's body, said securing pocket comprising:
  a receptacle formed between a flexible front panel and a flexible rear panel, said receptacle having left and right and top and bottom edges, said front and rear panels being joined together along said left and right and bottom edges while said top edge remains unbounded to access an interior region of said receptacle, said left and right edges each having a straight segment adjoining said top edge, the distance between said left and right edges comprising a pocket width ($W_p$), the distance between said bottom and top edges comprising a pocket height ($H_p$), said pocket width ($W_p$) being generally equal to said pocket height ($H_p$),
  a flap extending from said rear panel adjacent said top edge of said receptacle, said flap having a flap width ($W_f$) generally equal to said pocket width ($W_p$), said flap having a flap height ($H_f$) that is between about 0.5 and 1.0 times said pocket height ($H_p$), a portion of said flap adjacent said top edge of said receptacle comprising a hinge, first and second pin eyelets formed along said hinge,
  an anchoring device operatively disposed through said first and second pin eyelets, said anchoring device comprising a safety pin,
  a connector operatively disposed between said flap and said front panel of said receptacle for releasably securing said flap to said receptacle in an overlapping relationship, said connector comprising a first part and a mating second part, said first part fixedly attached to said flap and said second part fixedly attached to said front panel of said receptacle,
  said receptacle and said flap each being fabricated from a multi-layer fabric material, said multi-layer fabric material having a water-impermeable core,
  a jam cleat disposed along each of said left and right edges adjacent said top edge of said receptacle, each said jam cleat forming a breach in said receptacle configured to receive a tethered section of the medical tube and apply a progressive wedge force on the medical tube in response to a tensile force along the medical tube, each said jam cleat comprising a V-shaped notch integrally formed at the intersection of said front and rear panels, each said jam cleat having a length (L) that is between about 0.15 and 0.30 times said pocket height ($H_p$).

* * * * *